United States Patent
Lee et al.

(10) Patent No.: US 9,149,239 B2
(45) Date of Patent: Oct. 6, 2015

(54) APPARATUS AND METHOD FOR MEASURING MEDICAL INFORMATION PROVIDING THREE-DIMENSIONAL STEREOSCOPIC IMAGE

(71) Applicant: SAMSUNG ELECTRONICS CO., LTD., Suwon-si (KR)

(72) Inventors: Kang Eui Lee, Seoul (KR); Young Hun Sung, Hwaseong-si (KR); Myung Jin Jung, Seoul (KR); Jong Ha Lee, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 289 days.

(21) Appl. No.: 13/860,196

(22) Filed: Apr. 10, 2013

(65) Prior Publication Data

US 2014/0112430 A1 Apr. 24, 2014

(30) Foreign Application Priority Data

Oct. 19, 2012 (KR) .................. 10-2012-0116850

(51) Int. Cl.
*G21K 4/00* (2006.01)
*A61B 6/02* (2006.01)
*A61B 6/00* (2006.01)

(52) U.S. Cl.
CPC .............. *A61B 6/022* (2013.01); *A61B 6/4014* (2013.01); *A61B 6/4417* (2013.01); *A61B 6/4441* (2013.01); *A61B 6/466* (2013.01); *A61B 6/504* (2013.01)

(58) Field of Classification Search
CPC ...... G06T 15/00; A61B 6/022; A61B 6/4014; A61B 6/4417; A61B 6/4441; A61B 6/466; A61B 6/504; A61B 6/4028; A61B 6/481; A61B 6/541; A61B 19/00; A61B 19/5225; A61B 2019/5291; A61B 5/055; A61B 6/032; A61B 6/4007; A61B 6/463; A61B 2576/023; A61B 6/035; A61B 6/04
USPC .................................... 378/4, 9, 41
See application file for complete search history.

(56) References Cited

U.S. PATENT DOCUMENTS

| | | | |
|---|---|---|---|
| 5,107,528 A * | 4/1992 | Asahina et al. | 378/98.2 |
| 2005/0119565 A1* | 6/2005 | Pescatore | 600/429 |
| 2008/0095308 A1* | 4/2008 | Kano | 378/41 |
| 2008/0095423 A1 | 4/2008 | Redel et al. | |
| 2009/0190717 A1 | 7/2009 | Kargar et al. | |
| 2009/0238334 A1* | 9/2009 | Brahme et al. | 378/41 |
| 2009/0257551 A1* | 10/2009 | Dafni et al. | 378/6 |
| 2009/0285355 A1* | 11/2009 | Brada et al. | 378/20 |
| 2011/0037761 A1 | 2/2011 | Mistretta et al. | |
| 2011/0044525 A1* | 2/2011 | Ohishi | 382/132 |
| 2013/0230136 A1* | 9/2013 | Sakaguchi et al. | 378/41 |

FOREIGN PATENT DOCUMENTS

| | | |
|---|---|---|
| JP | 2006-296707 A | 11/2006 |
| JP | 2007-125374 A | 5/2007 |
| JP | 2007-244865 A | 9/2007 |
| JP | 2010-207591 A | 9/2010 |
| KR | 10-2001-0060301 A | 7/2001 |

* cited by examiner

*Primary Examiner* — Irakli Kiknadze
(74) *Attorney, Agent, or Firm* — Sughrue Mion, PLLC

(57) ABSTRACT

An apparatus and method for providing a 3D stereoscopic image is provided. The apparatus may provide a 3D stereoscopic image generated based on two projection images imaged at different positions.

21 Claims, 6 Drawing Sheets

TO 220

APPARATUS AND METHOD FOR MEASURING MEDICAL INFORMATION PROVIDING THREE-DIMENSIONAL STEREOSCOPIC IMAGE

CROSS-REFERENCE TO RELATED APPLICATION

This application claims priority from Korean Patent Application No. 10-2012-0116850, filed on Oct. 19, 2012, in the Korean Intellectual Property Office, the entire disclosure of which is incorporated herein by reference.

BACKGROUND

1. Field

Methods and apparatuses consistent with exemplary embodiments relate to providing a three-dimensional (3D) stereoscopic image based on a measured medical information image.

2. Description of the Related Art

A digital biplane angiography system may be used for intervention treatments that treat diseases in an inoperable area using needles or narrow tubes. The digital biplane angiography system may be used for intervention treatments of various blood vessels, as for example, a blood vessel in a brain, and various organs.

A related art digital biplane angiography system may provide frontal projection images and lateral projection images of an object. Accordingly, a user may predict an inner shape and state of a body of the object, based on the projection images.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

According to an aspect of an exemplary embodiment, there may be provided a method of providing 3D medical information by a medical diagnostic apparatus, the method including generating a first projection image and a second projection image, generating a stereoscopic image based on the first projection image and the second projection image, and outputting the stereoscopic image using a 3D display, wherein the first projection image may be generated by a detector detecting an X-ray irradiated toward an object by a source at a first position, and the second projection image may be generated by the detector detecting an X-ray irradiated toward the object by the source at a second position.

The source and the detector may be disposed to face each other while the object is positioned between the source and the detector.

The generating of the first projection image and the second projection image may include moving the source from the first position to the second position.

The source and the detector may be connected to each other by a C-arm.

The movement of the source may correspond to a rotary movement produced along a circular orbit around the object.

A difference between the first position and the second position may be determined based on a baseline of a viewer provided with the stereoscopic image.

The source may include a first source and a second source.

The detector may include a first detector and a second detector.

The generating of the first projection image and the second projection image may include generating, by the first detector, the first projection image by detecting an X-ray irradiated toward the object by the first source, and generating, by the second detector, the second projection image by detecting an X-ray irradiated toward the object by the second source.

The first source and the first detector may provide a frontal projection image of the object, and the second source and the second detector may provide a lateral projection image of the object.

The generating of the first projection image and the second projection image may include generating, by the detector, a plurality of projection images by detecting X-rays irradiated toward the object by the source at a plurality of different positions, respectively, and selecting the first projection image and the second projection image from among the plurality of projection images, based on the baseline of the viewer.

According to an aspect of an exemplary embodiment, there may be provided an apparatus for providing 3D medical information, the apparatus including a source to irradiate an X-ray toward an object at a first position, and to irradiate an X-ray toward the object at a second position differing from the first position, a detector to generate a first projection image by detecting the X-ray irradiated by the source at the first position, and to generate a second projection image by detecting the X-ray irradiated by the source at the second position, a controller to generate a stereoscopic image based on the first projection image and the second projection image, and an output unit to output the stereoscopic image.

The controller may determine a difference between the first position and the second position, based on a baseline of a viewer provided with the stereoscopic image.

The source may include a first source and a second source.

The detector may include a first detector and a second detector.

The first detector may generate the first projection image by detecting an X-ray irradiated toward the object by the first source.

The second detector may generate the second projection image by detecting an X-ray irradiated toward the object by the second source.

The 3D medical information providing apparatus may provide a two-dimensional (2D) mode.

In the 2D mode, the first source and the first detector may provide a frontal projection image of the object, and the second source and the second detector may provide a lateral projection image of the object.

The source may irradiate X-rays toward the object at a plurality of different positions, respectively, and the detector may generate a plurality of projection images by detecting the X-rays irradiated toward the object by the source at the plurality of different positions, respectively.

The controller may generate the first projection image and the second projection image, by selecting the first projection image and the second projection image from among the plurality of projection images.

BRIEF DESCRIPTION OF THE DRAWINGS

The above and/or other aspects of exemplary embodiments will become apparent by describing certain exemplary embodiments, with reference to the accompanying drawings, in which.

DETAILED DESCRIPTION

Figure 1:
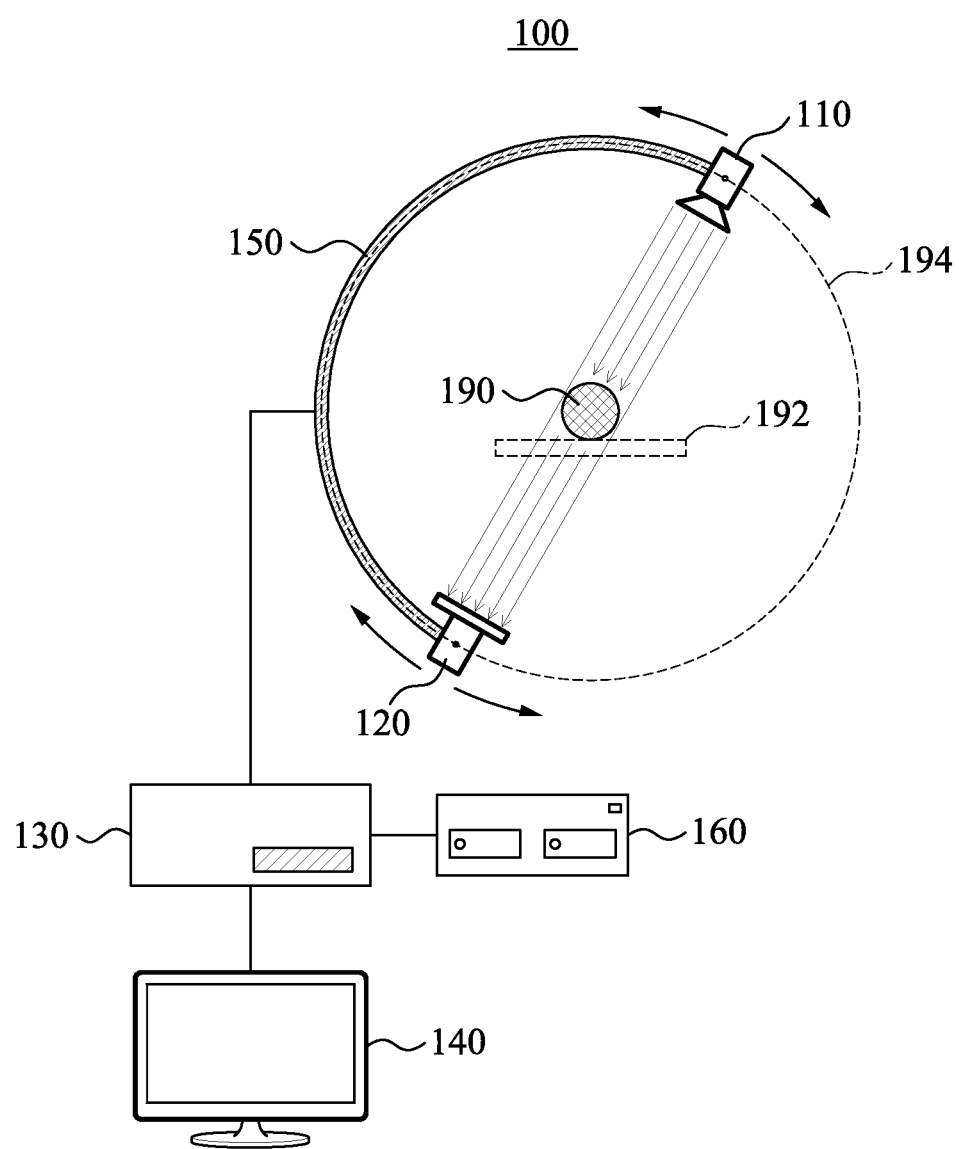
FIG. 1 illustrates an apparatus for providing 3D medical information according to an exemplary embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

FIG. 1 illustrates an apparatus 100 for providing 3D medical information according to an exemplary embodiment.

Referring to FIG. 1, the apparatus 100 for providing 3D medical information may include a source 110, a detector 120, a controller 130, and an output unit 140, i.e., a display. Hereinafter, the apparatus 100 for providing 3D medical information will be referred to as the apparatus 100 for brevity and ease of description. The apparatus 100 may correspond to a biplane angiography system.

In FIG. 1, a cross section 190 of an object is illustrated. The object may refer to an object to be imaged by the apparatus 100 or a measurement object. In addition, a cross section 192 of a gantry on which the object is positioned is illustrated. The gantry may be used to place the object at a position suitable for being imaged.

The source 110 may irradiate an X-ray toward the object. The detector 120 may detect the irradiated X-ray, thereby generating a projection image of the object. The X-ray is provided as an example. Depending on an exemplary embodiment, a predetermined signal used for obtaining medical information may replace the X-ray.

In order for the detector 120 to detect the X-ray irradiated by the source 110, the source 110 and the detector 120 may be disposed to face each other while the object is positioned between the source 110 and the detector 120.

The apparatus 100 may further include a C-arm 150. The source 110 and the detector 120 may be connected to each other by the C-arm 150. The C-arm 150 may move the source 110 and the detector 130. The movement may correspond to a rotary movement produced around the object. A dotted circle 194 indicates a trajectory of the source 110 and the detector 120 when the C-arm 150 rotates.

The C-arm 150 and the rotary movement are provided only as an example. The source 110 may be moved to a position suitable for irradiating an X-ray toward the object, by a predetermined mechanical apparatus or method other than the C-arm 150. The detector 120 may be moved to a position suitable for detecting the X-ray irradiated by the source 110, by a predetermined mechanical apparatus or method other than the C-arm 150.

The controller 130 may generate a stereoscopic image, based on at least one projection image generated by the source 110 and the detector 120. The stereoscopic image may correspond to a stereoscopic projection image. The stereoscopic image may provide 3D image information about the object to a viewer. The stereoscopic image may correspond to a 3D image providing information for a medical diagnosis with respect to an object. The viewer may refer to a user operating the apparatus 100, for example, a medical professional.

The output unit 140 may output the generated stereoscopic image. The output unit 140 may correspond to a 3D display providing a user with a 3D image.

For example, when the viewer wears a special type of eyewear, for example, shutter-glasses, the output unit 140 may be synchronized with the eyewear to alternatively output an image visible to a left eye of the viewer and an image visible to a right eye of the viewer. The image visible to the left eye of the viewer may refer to an image output when a shutter of a right lens of the eyewear is closed, and the image visible to the right eye of the viewer may refer to an image output when a shutter of a left lens of the eyewear is closed. In this instance, the stereoscopic image may correspond to an image generated when two projection images are repeated alternatively. A storage 160 may store projection images. The storage 160 may provide the stored images to the controller 130.

When the viewer wears polarized eyewear, the output unit 140 may output an image to be viewed through a left polarized lens and an image to be viewed through a right polarized lens. The image to be viewed through the left polarized lens may refer to an image passing through a filter of the left polarized lens, and the image to be viewed through the right polarized lens may refer to an image passing through a filter of the right polarized lens. The output unit 140 may include two displays. When the viewer brings the left eye and the right eye of the viewer close to the two displays, the viewer may view an image for a left eye and an image for a right eye on two displays, respectively. In this instance, the stereoscopic image may correspond to two projection images.

The aforementioned projection image and the stereoscopic image may correspond to a video. In particular, the projection image may correspond to a video generated by imaging the object by successive image acquisitions.

Figure 2:
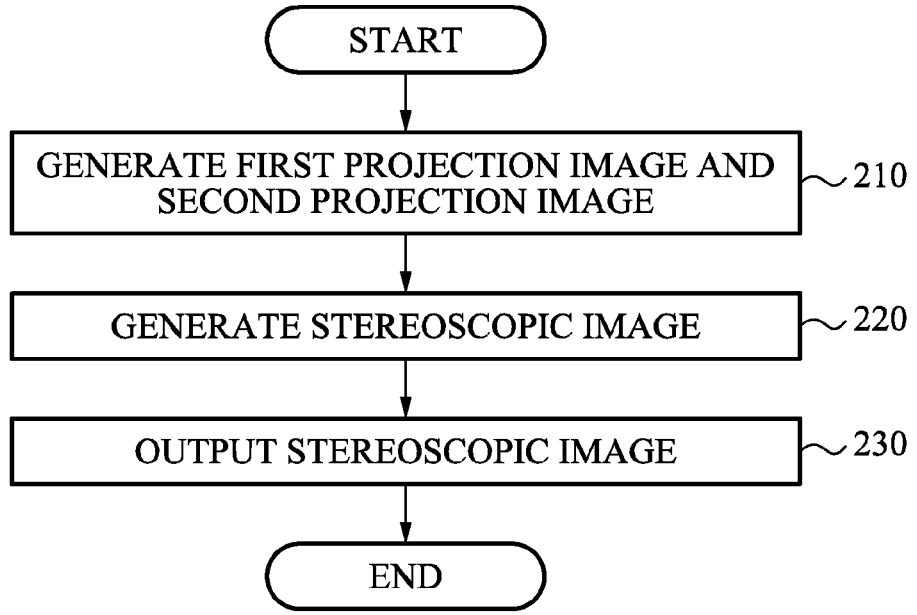
FIG. 2 illustrates a method of providing 3D medical information according to an exemplary embodiment.

FIG. 2 illustrates a method of providing 3D medical information according to an exemplary embodiment.

Referring to FIG. 2, in operation 210, the source 110 and the detector 120 may generate a first projection image and a second projection image.

The source 110 may irradiate an X-ray toward an object at a first position. The detector 120 may generate the first projection image, by detecting the X-ray irradiated by the source 110 at the first position. In particular, the first projection image may be generated by the detector 120 detecting the X-ray irradiated toward the object by the source 110 at the first position.

The source 110 may irradiate an X-ray toward the object at a second position. The second position may differ from the first position. The detector 120 may generate the second projection image, by detecting the X-ray irradiated by the source 110 at the second position. In particular, the second projection image may be generated by the detector 120 detecting the X-ray irradiated toward the object by the source 110 at the second position.

The controller 130 may determine the first position and the second position, respectively. The controller 130 may determine the first position and the second position, respectively, based on a control of a viewer of a stereoscopic image. The viewer may determine a portion of the object desired to be observed, and may determine a portion of the object to be projected in the stereoscopic image, and an angle for projecting the portion of the object. The viewer may control the controller 130 such that the portion of the object desired to be observed may be displayed in the stereoscopic image. The controller 130 may determine the first position and the second position, based on the control. When it is assumed that the viewer views the portion of the object in real time, an image at the first position may correspond to an image to be focused toward one of the eyes of the viewer. An image at the second position may correspond to an image to be focused toward the other eye of the viewer. Accordingly, the viewer may view the portion of the object with a 3D effect, through the stereoscopic image including the image at the first position and the image at the second position.

A difference between the first position and the second position may be changed based on a baseline of the viewer. The baseline may refer to a distance between the eyes of the viewer. For example, as the baseline of the viewer increases, a distance between the first position and the second position may be increased. The controller 130 may determine the difference between the first position and the second position, based on the baseline of the viewer who views a stereoscopic image. For example, the controller 130 may determine the distance between the first position and the second position to be proportional to a length of the baseline of the viewer, i.e., a distance between the eyes.

The controller 130 may use a preset value or a value input by the viewer, as the baseline or the length of the baseline.

In operation 220, the controller 130 may generate a stereoscopic image, based on the first projection image and the second projection image. The controller 130 may generate the stereoscopic image, by applying specific processing to the first projection image and the second projection image, respectively. The specific processing may refer to the processing for enabling a projection image to be suitable for being output by the output unit 140, or for being viewed by the viewer.

In operation 230, the output unit 140 may output the generated stereoscopic image. The controller 130 may output the stereoscopic image, using the output unit 140 corresponding to a 3D display.

The description provided with reference to FIG. 1 may be applied identically and thus, a repeated description will be omitted.

Figure 3:
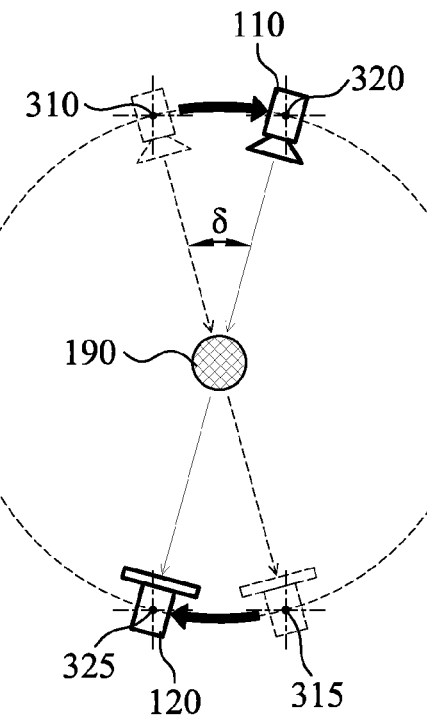
FIG. 3 illustrates a method of generating a first projection image and a second projection image according to an exemplary embodiment.

FIG. 3 illustrates a method of generating a first projection image and a second projection image according to an exemplary embodiment.

Referring to FIG. 3, the source 110 and the detector 120 may move, respectively. In FIG. 3, the source 110 may move from a first position 310 to a second position 320. The detector 120 may move from a third position 315 corresponding to the first position 310 to a fourth position 325 corresponding to the second position 320. The position of the detector 120 corresponding to the position of the source 110 may refer to a position suitable for the detector 120 to detect an X-ray irradiated by the source and passed through the object. When the source 110 and the detector 120 are connected to the C-arm 150, the source 110 may move along with the C-arm 150 and the detector 120 may move together to a position corresponding to a position of the source 110 when the C-arm 150 moves.

In FIG. 3, the source 110 and the detector 120 may move along a circular orbit around the object. Such a movement may refer to a movement produced when the source 110 and the detector 120 are connected to the C-arm 150 and the C-arm 150 rotates around the object. However, the movement is provided as an example, and a predetermined apparatus or method for moving the source 110 and the detector 120, respectively, may be used.

Figure 4:
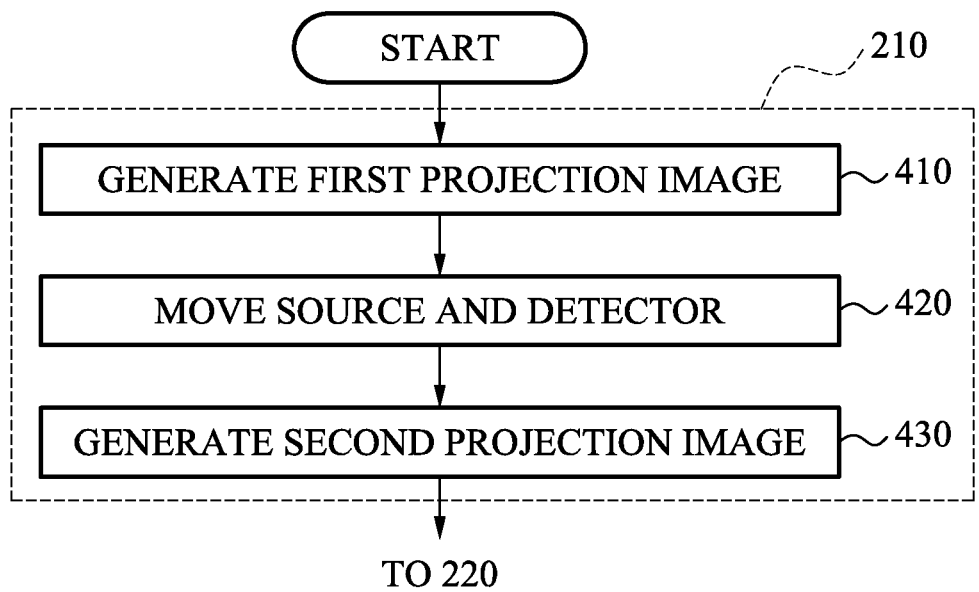
FIG. 4 illustrates a method of generating a first projection image and a second projection image according to an exemplary embodiment.

FIG. 4 illustrates a method of generating a first projection image and a second projection image according to an exemplary embodiment.

The operation 210 described above with reference to FIG. 2 may include operations 410 through 430.

Referring to FIG. 4, in operation 410, the source 110 may irradiate an X-ray toward an object at a first position. The detector 120 may generate a first projection image, by detecting the X-ray irradiated by the source 110 at the first position.

In operation 420, the source 110 may move from the first position to a second position. The movement may correspond to a rotary movement provided along a circular orbit around the object.

The detector 120 may move from a position corresponding to the first position to a position corresponding to the second position.

In operation 430, when the source 110 irradiates an X-ray toward the object at the second position, the detector 120 may generate a second projection image, by detecting the X-ray irradiated by the source 110 at the second position.

The controller 130 may adjust a rotation angle $\delta$ of the C-arm 150, in proportion to a length of a baseline of a viewer. The controller 130 may move the source 110, based on the baseline of the viewer.

The descriptions provided with reference to FIGS. 1 through 3 may be applied here and thus, a repeated description will be omitted.

Figure 5:
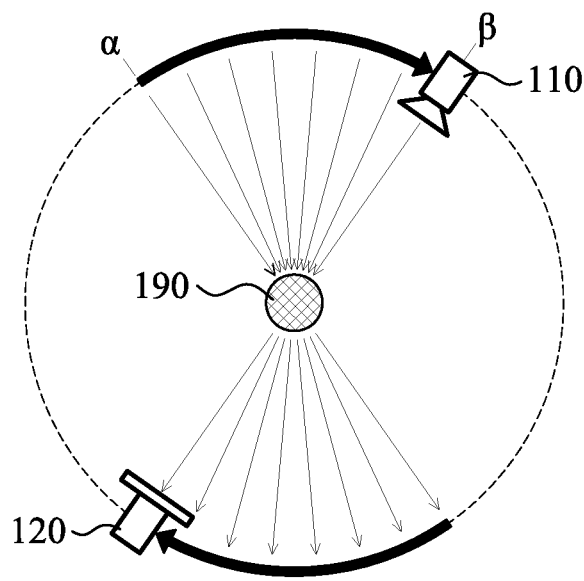
FIG. 5 illustrates a method of generating a first projection image and a second projection image according to an exemplary embodiment.

FIG. 5 illustrates a method of generating a first projection image and a second projection image according to an exemplary embodiment.

Referring to FIG. 5, the source 110 and the detector 120 may move continuously. In FIG. 5, the source 110 may move from a position corresponding to a first angle $\alpha$ to a position corresponding to a second angle $\beta$. The detector 120 may move to a position corresponding to the position of the source 110, based on the movement of the source 110.

During the movement, the source 110 and the detector 120 may generate a plurality of projection images. The source 110 may irradiate X-rays toward the object at a plurality of positions differing from each other, respectively. The detector 120 may generate the plurality of projection images, by detecting the X-rays irradiated toward the object by the source 110 at the plurality of positions, respectively. The plurality of projection images may correspond to the plurality of positions, respectively.

The storage 160 may store the plurality of projection images generated. The storage 160 may receive the plurality of projection images from the detector 120 or the controller 130.

The controller 130 may select a first projection image and a second projection image from among the plurality of projection images. The controller 130 may request the images selected as the first projection image and the second projection image, among the plurality of projection images, from the storage 160. The storage 160 may transmit, to the controller 130, the projection images requested by the controller 130, among the plurality of projection image stored.

Figure 6:
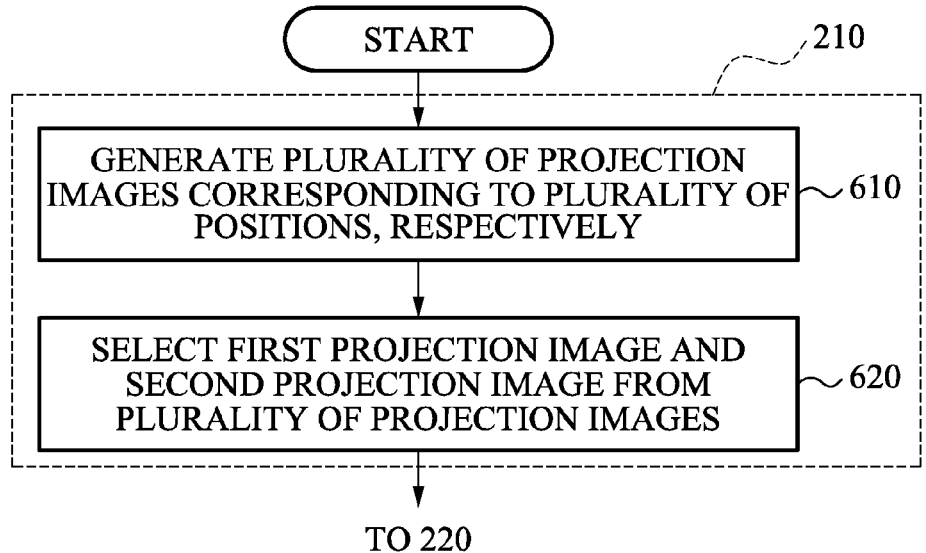
FIG. 6 illustrates a method of generating a first projection image and a second projection image according to an exemplary embodiment.

FIG. 6 illustrates a method of generating a first projection image and a second projection image according to an exemplary embodiment.

The operation 210 described above with reference to FIG. 2 may include operations 610 through 620.

Referring to FIG. 6, in operation 610, the source 110 and the detector 120 may move continuously, respectively. During the movement, the source 110 may irradiate X-rays toward the object at a plurality of positions differing from each other, respectively. The detector 120 may generate a plurality of projection images, by detecting the X-rays irradiated toward the object by the source 110 at the plurality of positions, respectively.

In operation 620, the controller 130 may generate a first projection image and a second projection image, by selecting the first projection image and the second projection image from among the plurality of projection images.

The descriptions provided with reference to FIGS. 1 through 5 may be applied here and thus, a repeated description will be omitted.

Figure 7:
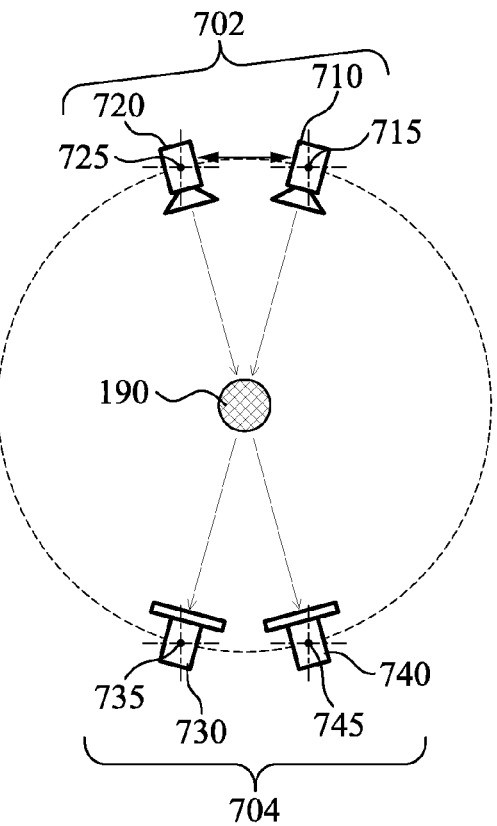
FIG. 7 illustrates a method of generating a first projection image and a second projection image using a plurality of sources and detectors according to an exemplary embodiment.

FIG. 7 illustrates a method of generating a first projection image and a second projection image using a plurality of sources and detectors according to an exemplary embodiment.

Referring to FIG. 7, a plurality of sources 702 and a plurality of detectors 704 may be provided. In FIG. 7, the plurality of sources 702 may include the first source 710 and the second source 720, and the plurality of detectors 704 may include the first source 730 and the second detector 740.

The first source 710 and the second source may irradiate X-rays toward the object at different positions, respectively. The first detector 730 and the second detector 740 may detect the X-rays irradiated by the first source 710 and the second source 720, respectively. A first position 715 of the first source 710 may differ from a second position 725 of the second source 720. A position 735 of the first detector 730 may be a position corresponding to the first position 715 of the first source 710. A position 745 of the second detector 740 may be a position corresponding to the second position 725 of the second source 720.

The operation 210 described with reference to FIG. 2 including generating a first projection image, and generating a second projection image is applicable, as described below.

In the generating of the first projection image, the first source 710 may irradiate an X-ray toward the object at the first position 715, and the first detector 730 may generate the first projection image, by detecting the X-ray irradiated toward the object by the first source 710 at the position 735 corresponding to the first position 715.

In the generating of the second projection image, the second source 720 may irradiate an X-ray toward the object at the second position 725, and the second detector 740 may generate the second projection image, by detecting the X-ray irradiated toward the object by the second source 720 at the position 745 corresponding to the second position 725.

The descriptions provided with reference to FIGS. 1 through 6 may be applied here and thus, a repeated description will be omitted.

Figure 8:
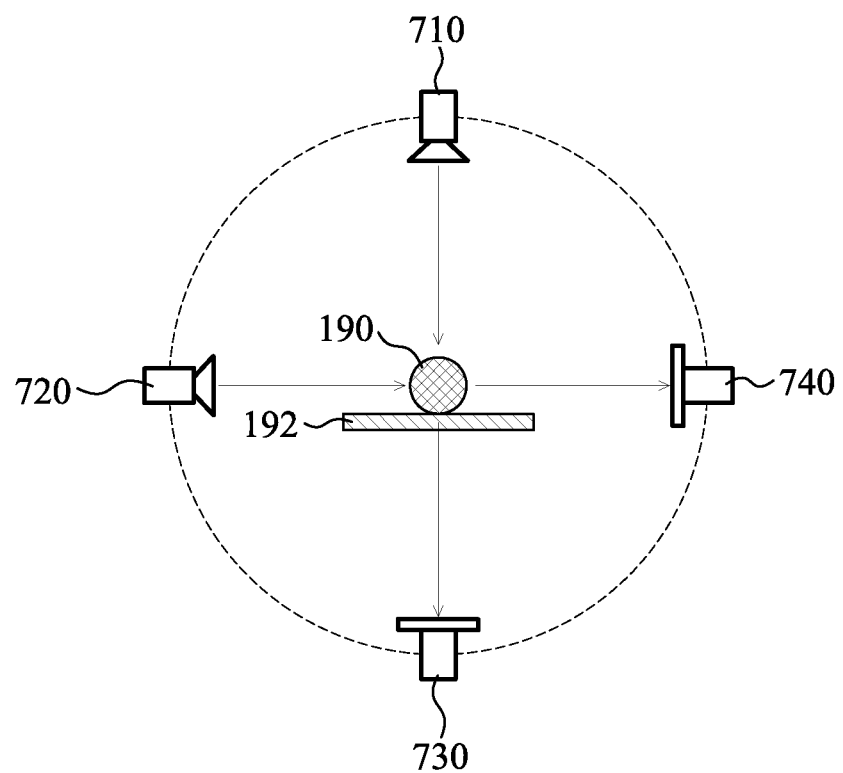
FIG. 8 illustrates a 2D mode according to an exemplary embodiment.

FIG. 8 illustrates a 2D mode according to an exemplary embodiment.

In exemplary embodiments described with reference to FIGS. 1 through 7, the controller 130 and the output unit 140 may provide a stereoscopic image. A mode in which a stereoscopic image is provided may be referred as a 3D mode of the apparatus 100 of FIG. 1.

The apparatus 100 may provide a 2D mode in addition to the 3D mode. In the 2D mode, the controller 130 and the output unit 140 may provide at least one 2D image. The at least one 2D image may correspond to at least one projection image generated at different positions, respectively. The different positions may refer to a position of the source and a position of the detector corresponding to the position of the source 110.

In FIG. 8, the first source 710 and the first detector 730 may provide a frontal projection image of the object. The second source 720 and the second detector 740 may provide a lateral projection image of the object. The frontal projection image may refer to a projection image of a frontal face of the object, and the lateral projection image may refer to a projection image of a lateral face of the object. The controller 130 may process or adjust the frontal projection image and the lateral projection image in a form suitable for being output by the controller 130 or the output unit 140. The output unit 140 may output the processed or adjusted frontal projection image and lateral projection image. The output unit 140 may output the processed or adjusted frontal projection image and lateral projection image, simultaneously or sequentially, and may output a projection image selected by a viewer from among the processed or adjusted frontal projection image and lateral projection image.

The descriptions provided with reference to FIGS. 1 through 7 may be applied here and thus, a repeated description will be omitted.

Figure 9:
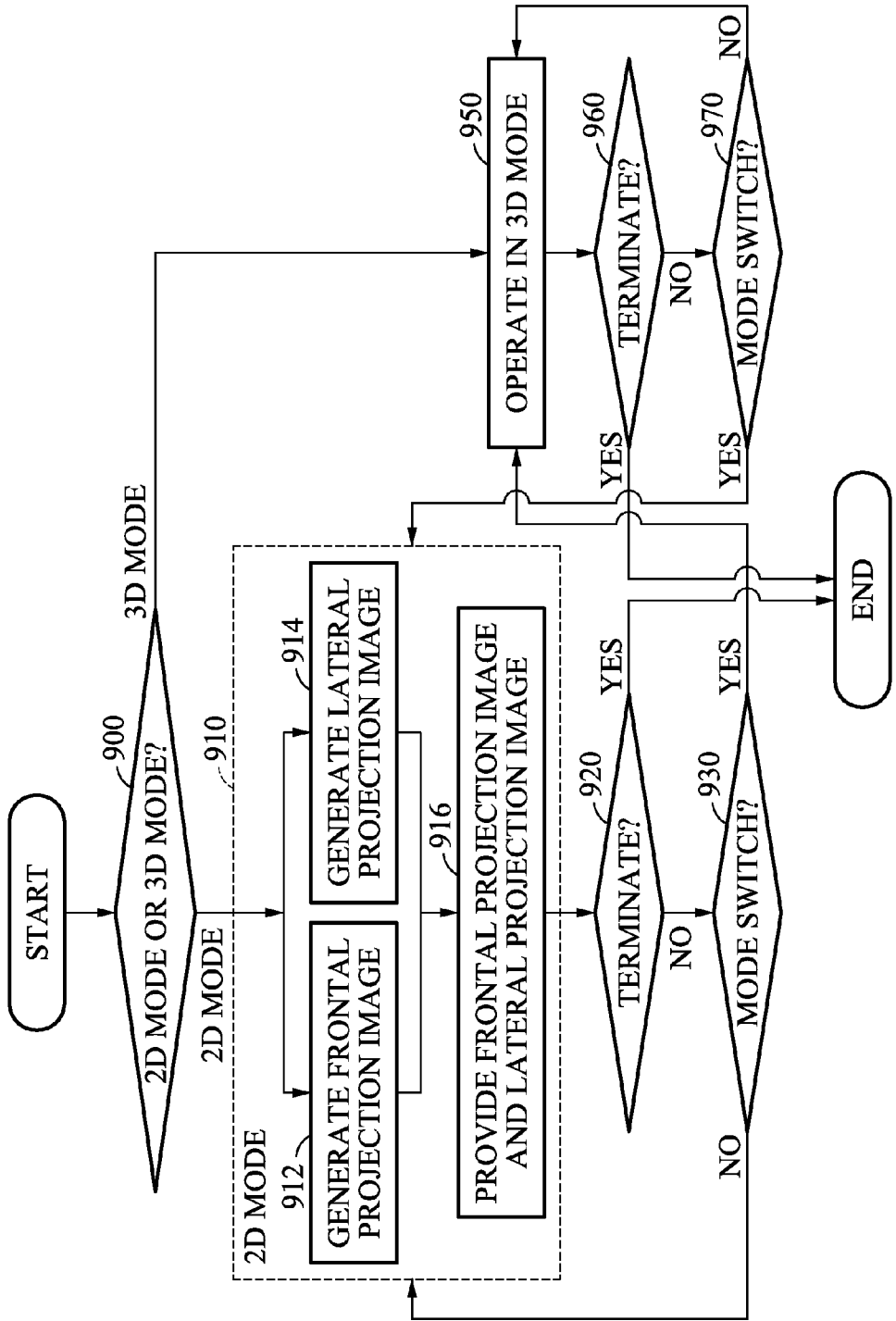
FIG. 9 illustrates an operation of an apparatus for providing 3D medical information according to an exemplary embodiment.

FIG. 9 illustrates an operation of an apparatus for providing 3D medical information according to an exemplary embodiment.

Referring to FIG. 9, in operation 900, the controller 130 may select a mode of the apparatus 100. When the controller 130 selects a 2D mode, operation 910 may be performed. When the controller 130 selects a 3D mode, operation 950 may be performed.

In operation 910, the apparatus 100 may operate in the 2D mode. The operation 910 may correspond to providing 2D medical information.

The operation 910 may include operations 912, 914, and 916.

In operation 912, the first source 710 may irradiate an X-ray toward the object in a frontal direction of the object, and the first detector 730 may generate a frontal projection image, by detecting the X-ray irradiated toward the object by the first source 710. Accordingly, in the 2D mode, the first source 710 and the first detector 730 may provide the frontal projection image of the object.

In operation 914, the second source 720 may irradiate an X-ray toward the object in a lateral direction of the object, and the second detector 740 may generate a lateral projection image, by detecting the X-ray irradiated toward the object by the second source 720. Accordingly, in the 2D mode, the second source 720 and the second detector 740 may provide the lateral projection image of the object.

In operation 916, the controller 130 and the output unit 140 may provide at least one of the frontal projection image and the lateral projection image.

In operation 920, the controller 130 may determine whether the operation of the apparatus 100 is to be terminated. When the operation is determined not to be terminated, operation 930 may be performed. When the operation is determined to be terminated, the procedure may be terminated.

In operation 930, the controller 130 may determine whether the mode is to be switched. When the mode is determined not to be switched, operation 910 may be repeated. When the mode is determined to be switched, operation 950 may be performed.

In operation 950, the apparatus 100 may operate in the 3D mode. The operation 950 may include the operations 210 through 230 described above with reference to FIG. 2.

In operation 960, the controller 130 may determine whether operation of the apparatus 100 is to be terminated. When operation of the apparatus 100 is determined not to be terminated, operation 970 may be performed. When the operation is determined to be terminated, the procedure may be terminated.

In operation 970, the controller 130 may determine whether the mode is to be switched. When the mode is determined not to be switched, operation 950 may be repeated. When the mode is determined to be switched, operation 910 may be performed.

The descriptions provided with reference to FIGS. 1 through 8 may be applied here and thus, a repeated description will be omitted.

According to exemplary embodiments described above, by using the source and the detector that are movable, the apparatus 100 may enable use of 3D stereoscopic X-rays and enable the viewer to perform a procedure with respect to imaging and/or measuring object rapidly and conveniently.

The method according to the above-described exemplary embodiments may be recorded in computer-readable media including program instructions to implement various operations embodied by a computer. The media may also include, alone or in combination with the program instructions, data files, data structures, and the like. Examples of computer-readable media include magnetic media such as hard disks, floppy disks, and magnetic tape; optical media such as CD ROM discs and DVDs; magneto-optical media such as optical discs; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules in order to perform the operations of the above-described exemplary embodiments, or vice versa.

Although a few exemplary embodiments have been shown and described, exemplary embodiments are not limited thereto. Instead, it would be appreciated by those skilled in the art that changes may be made to these exemplary embodiments without departing from the principles and spirit of the disclosure, the scope of which is defined by the claims and their equivalents.

What is claimed is:

1. A method of providing three-dimensional (3D) medical information by a medical diagnostic apparatus, the method comprising:
   generating a first projection image and a second projection image;
   generating a stereoscopic image based on the first projection image and the second projection image; and
   outputting the stereoscopic image using a 3D display,
   wherein the first projection image is generated by a detector detecting X-rays irradiated toward an object by a source at a first position,
   the second projection image is generated by the detector detecting X-rays irradiated toward the object by the source at a second position,
   wherein the first projection image and the second projection image correspond to a left-eye image and a right-eye image of a viewer,
   a difference amount between the first position and the second position is proportional to a baseline of the viewer provided with the stereoscopic image,
   the baseline of the viewer is a distance between a left eye and a right eye of the viewer, and
   at least one of the source and the detector is moved to the second position to irradiate the X-rays or to detect the X-rays, respectively, by the difference amount determined for the viewer.

2. The method of claim 1, wherein the source and the detector are disposed to face each other, and
   the object is positioned between the source and the detector.

3. The method of claim 1, wherein the generating the first projection image and the second projection image comprises moving the source from the first position to the second position, and
   an amount of a movement of the source is determined in proportion to the baseline of the viewer.

4. The method of claim 3, wherein the source and the detector are connected to each other by a C-arm.

5. The method of claim 3, wherein the movement of the source corresponds to a rotary movement along a circular orbit around the object.

6. The method of claim 1, wherein:
   the source comprises a first source and a second source,
   the detector comprises a first detector and a second detector, and
   the generating of the first projection image and the second projection image comprises:
   generating, by the first detector, the first projection image by detecting the X-rays irradiated toward the object by the first source; and
   generating, by the second detector, the second projection image by detecting the X-rays irradiated toward the object by the second source.

7. The method of claim 6, wherein the first source and the first detector provide a frontal projection image of the object, and the second source and the second detector provide a lateral projection image of the object.

8. The method of claim 1, wherein the generating the first projection image and the second projection image comprises:
   generating, by the detector, a plurality of projection images by detecting the X-rays irradiated toward the object by the source at a plurality of different positions; and
   selecting the first projection image and the second projection image from the plurality of projection images, based on a on the baseline of a viewer.

9. A non-transitory computer-readable medium comprising a program which when executed by a computer causes the computer to perform the method of claim 1.

10. The method of claim 1, wherein the outputting comprises displaying, to the viewer, alternatively the left-eye image and the right-eye image substantially simultaneously with the generating the first projection image and the second projection image.

11. An apparatus for providing three-dimensional (3D) medical information, the apparatus comprising:
- a source to irradiate X-rays toward an object at a first position, and at a second position different from the first position;
- a detector to generate a first projection image by detecting the X-rays irradiated by the source at the first position, and a second projection image by detecting the X-rays irradiated by the source at the second position;
- a controller to generate a stereoscopic image based on the first projection image and the second projection image; and
- an output unit to output the stereoscopic image,
- wherein the first projection image and the second projection image correspond to a left-eye image and a right-eye image of a viewer,
- a difference amount between the first position and the second position is proportional to a baseline of the viewer provided with the stereoscopic image,
- the baseline of the viewer is a distance between a left eye and a right eye of the viewer, and
- at least one of the source and the detector is moved to the second position to irradiate the X-rays or to detect the X-rays, respectively, by the difference amount determined for the viewer.

12. The apparatus of claim 11, wherein the source and the detector are disposed to face each other, and
- the object is positioned between the source and the detector.

13. The apparatus of claim 11, wherein the source moves from the first position to the second position, and
- an amount of a movement of the source is determined in proportion to the baseline of the viewer.

14. The apparatus of claim 13, wherein the source and the detector are connected to each other by a C-arm.

15. The apparatus of claim 13, wherein a movement of the source corresponds to a rotary movement along a circular orbit around the object.

16. The apparatus of claim 11, wherein:
- the source comprises a first source and a second source,
- the detector comprises a first detector and a second detector,
- the first detector generates the first projection image by detecting the X-rays irradiated toward the object by the first source, and
- the second detector generates the second projection image by detecting the X-rays irradiated toward the object by the second source.

17. The apparatus of claim 16, wherein:
- the 3D medical information providing apparatus provides a two-dimensional (2D) mode, and
- the first source and the first detector provide a frontal projection image of the object, and the second source and the second detector provide a lateral projection image of the object, in the 2D mode.

18. The apparatus of claim 11, wherein:
- the source irradiates the X-rays toward the object at a plurality of different positions,
- the detector generates a plurality of projection images by detecting the X-rays irradiated toward the object by the source at the plurality of different positions, and
- the controller generates the first projection image and the second projection image, by selecting the first projection image and the second projection image from the plurality of projection images.

19. A method comprising:
- irradiating X-rays onto a region of interest (ROI) of an object at a first position;
- generating a first projection image by detecting the X-rays passed through the object;
- irradiating X-rays onto the object at a second position disposed at a first distance from the first position;
- generating a second projection image by detecting the X-rays passed through the object;
- generating a stereoscopic image of the ROI based on the first projection image and the second projection image; and
- providing a three-dimensional (3D) display of the stereoscopic image,
- wherein the irradiating the X-rays onto the object at the second position comprises:
- prior to the irradiating the X-rays onto the object at the second position, determining a second distance between eyes of a user, and
- determining the first distance as a distance proportional to the second distance.

20. The method of claim 19, wherein the first position and the second position are disposed along a same trajectory extending around the object.

21. The method of claim 19, wherein the ROI comprises a vascular region comprising vascular structures, and the method further comprises performing measurements with respect to the vascular structures.

* * * * *